United States Patent
Kanno

(10) Patent No.: US 9,540,742 B2
(45) Date of Patent: Jan. 10, 2017

(54) BACTERICIDAL WATER GENERATING SYSTEM AND METHOD OF BACTERICIDAL WASHING

(71) Applicant: Minoru Kanno, Sendai (JP)

(72) Inventor: Minoru Kanno, Sendai (JP)

(*) Notice: Subject to any disclaimer, the term of this patent is extended or adjusted under 35 U.S.C. 154(b) by 85 days.

(21) Appl. No.: 14/397,982

(22) PCT Filed: Apr. 23, 2013

(86) PCT No.: PCT/JP2013/061833
§ 371 (c)(1),
(2) Date: Oct. 30, 2014

(87) PCT Pub. No.: WO2014/010291
PCT Pub. Date: Jan. 16, 2014

(65) Prior Publication Data
US 2015/0125344 A1 May 7, 2015

(30) Foreign Application Priority Data
Jul. 13, 2012 (JP) ................. 2012-158119

(51) Int. Cl.
*A61L 2/18* (2006.01)
*C25B 15/08* (2006.01)
(Continued)

(52) U.S. Cl.
CPC .............. *C25B 15/08* (2013.01); *A23L 3/3454* (2013.01); *A23L 3/3589* (2013.01); *C02F 1/4618* (2013.01);
(Continued)

(58) Field of Classification Search
CPC ................ A23L 3/3454; A61L 2/18
See application file for complete search history.

(56) References Cited

U.S. PATENT DOCUMENTS 5,676,760 A * 10/1997 Aoki ................ B08B 3/08
134/1.3
5,938,916 A 8/1999 Bryson et al.
(Continued)

FOREIGN PATENT DOCUMENTS

DE 10051180 A1 8/2002
EP 2065342 A1 6/2009
(Continued)

OTHER PUBLICATIONS

Becking et al., "Limits of the Natural Environment in Terms of pH and Oxidation-Reduction Potentials," *The Journal of Geology*, May 1960, vol. 68 No. 3, pp. 243-284.
(Continued)

*Primary Examiner* — Sean E Conley
*Assistant Examiner* — Donald Spamer
(74) *Attorney, Agent, or Firm* — Oliff PLC

(57) ABSTRACT

A bactericidal water generating system and a method of bactericidal washing which can enhance the bactericidal capacity and washing effect of acidic electrolyzed water. An electrolyzer electrolyzes a chloride-containing aqueous electrolyte solution to generate acidic electrolyzed water, the aqueous electrolyte being pre-adjusted to pH 3 to 5 with a pH adjuster. An acidic water container is connected to the electrolyzer, and stores the acidic electrolyzed water generated by the electrolyzer. A gaseous chlorine circulator collects gaseous chlorine generated from the acidic electrolyzed water in the acidic water container, and the gaseous chlorine collected is supplied to the acidic electrolyzed water in the acidic water container by bubbling. A transition metal supply unit is provided so that a transition metal-containing solution can be supplied to the inside of the acidic water container.

14 Claims, 12 Drawing Sheets

(a)

(b)

(51) Int. Cl.
  *A23L 3/3454* (2006.01)
  *C02F 1/461* (2006.01)
  *C02F 1/467* (2006.01)
  *A23L 3/3589* (2006.01)
  *C25B 1/26* (2006.01)

(52) U.S. Cl.
  CPC .............. *C02F 1/4674* (2013.01); *C25B 1/26* (2013.01); *A61L 2/18* (2013.01); *A61L 2202/11* (2013.01); *A61L 2202/17* (2013.01); *C02F 2001/46185* (2013.01)

(56) References Cited

U.S. PATENT DOCUMENTS

| | | | |
|---|---|---|---|
| 6,610,249 | B1 * | 8/2003 | Hinze .................... A23B 4/015 422/28 |
| 2003/0141202 | A1 | 7/2003 | Nakamura et al. |
| 2003/0146108 | A1 | 8/2003 | Nakamura et al. |
| 2003/0164309 | A1 | 9/2003 | Nakamura et al. |
| 2006/0124444 | A1 | 6/2006 | Nakamura et al. |
| 2006/0163085 | A1 | 7/2006 | Hanaoka |
| 2006/0288743 | A1 | 12/2006 | van Kralingen et al. |
| 2008/0047844 | A1 | 2/2008 | Miyashita |
| 2009/0148341 | A1 | 6/2009 | Kanno et al. |
| 2011/0253549 | A1 | 10/2011 | Kanno |

FOREIGN PATENT DOCUMENTS

| | | |
|---|---|---|
| JP | A-8-132050 | 5/1996 |
| JP | A-8-155459 | 6/1996 |
| JP | A-9-103786 | 4/1997 |
| JP | A-9-124431 | 5/1997 |
| JP | A-10-118655 | 5/1998 |
| JP | A-11-221569 | 8/1999 |
| JP | A-2000-218269 | 8/2000 |
| JP | A-2002-316163 | 10/2002 |
| JP | A-2003-259755 | 9/2003 |
| JP | A-2004-25123 | 1/2004 |
| JP | A-2004-267956 | 9/2004 |
| JP | A-2006-204235 | 8/2006 |
| JP | A-2008-49317 | 3/2008 |
| JP | A-2008-68239 | 3/2008 |
| JP | A-2009-195862 | 9/2009 |
| JP | A-2009-255068 | 11/2009 |
| JP | A-2010-201081 | 9/2010 |

OTHER PUBLICATIONS

Hotta, "Use of Functional Water—the Bactericidal Mechanism and Applications of Strongly Acidic Electrolyzed Water," *Food Processing and Ingredients*, 1998, vol. 33, pp. 5-7 (with translation).

Iwasawa et al., "Bactericidal Effect of Acidic Electrolyzed Water—Comparison of Chemical Acidic Sodium Hydrochloride (NaOCl) Solution," *The Journal of the Japanese Association for Infectious Diseases*, 1996, vol. 70, pp. 915-922 (with abstract).

Tsuchiya et al., "A Critical Review on the Chemical Bactericidal Factors of the Acidic Electrolyzed Water," *Bulletin of Science and Engineering Takushoku University*, 2004, vol. 9 pp. 21-30 (with abstract).

Yonemori et al., "Analysis of Hydoxyl Radical Generated in Electrolyzed Strong Acid Aqueous Solution by Electron Spin Resonance Spectroscopy," *Journal of the Chemical Society of Japan*, 1997, No. 7, pp. 497-501 (with abstract).

Suzuki et al., "Observation of Oxygenic Radicals in High Oxidation Potential Water," *The Japanese Journal of Conservative Dentistry*, 1998, vol. 41 No. 5, pp. 975-982 (with abstract).

Tsuchiya et al., "Characterization of Chemical Factors as the Bactericidal Basis of Acidic Denkaisui," *Kinousui Kenkyu*, 2004, vol. 2 No. 2, pp. 75-79 (with abstract).

International Search Report issued in PCT/JP2013/061833 mailed Aug. 6, 2013.

Oct. 8, 2015 Extended Search Report issued in European Patent Application No. 13816821.6.

* cited by examiner

Fig.1
(a)
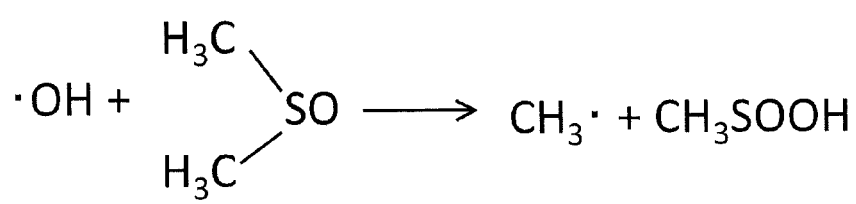
(b)
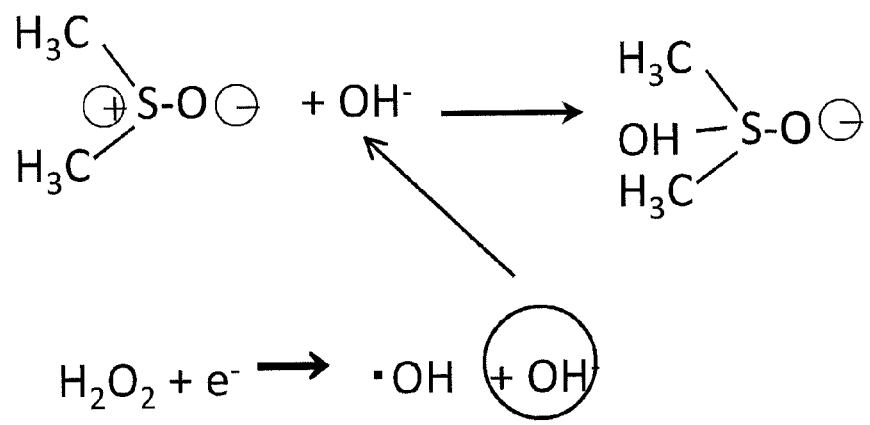

(a) Electrolyzed once (b) + FeSO$_4$ 331.277   336.277   341.277
magnetic field (mT)

Fig.10
(a) 0 M sodium formate
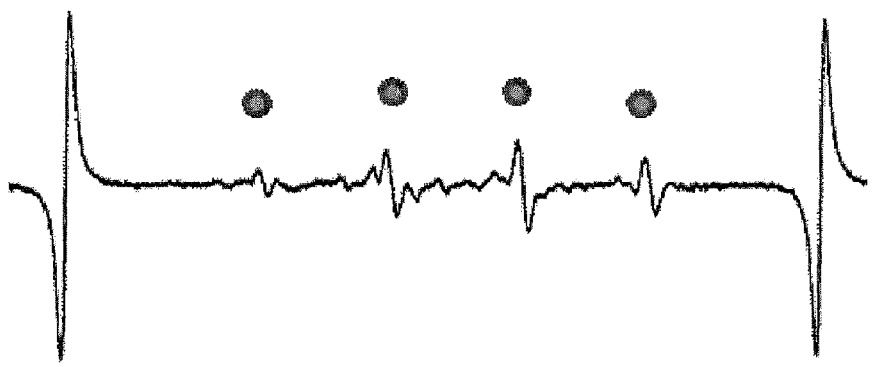
(b) 100 mM sodium formate
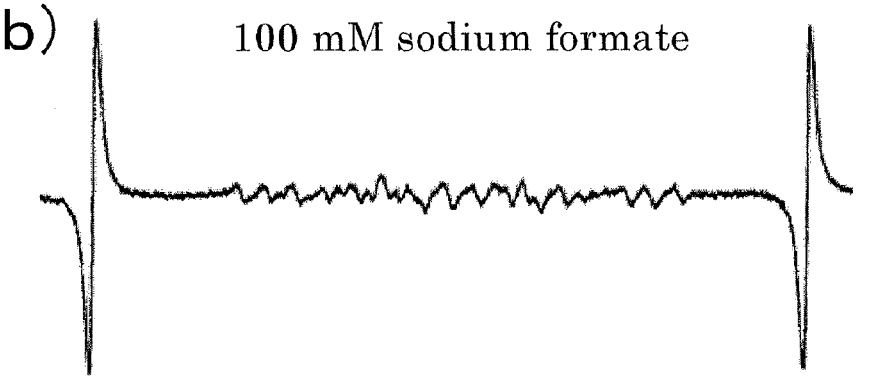
331.277　　　　　　　336.277　　　　　　　341.277
magnetic field (mT)

BACTERICIDAL WATER GENERATING SYSTEM AND METHOD OF BACTERICIDAL WASHING

TECHNICAL FIELD

The present invention relates to a bactericidal water generating system and a method of bactericidal washing.

BACKGROUND ART

In recent years, strongly acidic electrolyzed water generated at an anode side upon electrolysis of a diluted solution of sodium chloride and the like has attracted attention in various fields because it shows a powerful bactericidal effect. Factors that strongly acidic electrolyzed water shows a bactericidal capacity include the followings: characteristic values, a low pH of pH 2.7 or less and a high ORP of +1100 mV or more, for strongly acidic electrolyzed water are outside the viable ranges, ORP +900 to −400 mV and pH 3 to 10 for microorganism (for example, see Nonpatent Literature 1). However, according to subsequent studies, currently popular theory is that it is due to the oxidizing power of effective chlorine which primarily comprises hypochlorous acid generated upon electrolysis (for example, see Nonpatent Literatures 2 or 3).

Radical species generated at an electrode are thought not to be involved in the bactericidal activity of strongly acidic electrolyzed water (for example, see Nonpatent Literature 4). That is, in general, a radical is highly reactive, unstable and short-lived since it has an unpaired electron. A hydroxyl radical is highly reactive and short-lived among others, and often attributed to be an agent of the activity of acidic electrolytic water. However, it is thought that a hydroxyl radical cannot be a basis for the bactericidal activity of acidic electrolyzed water because a signal from a hydroxyl radical was not detected in the analysis using the electron spin resonance (ESR) spin trap method (for example, see Nonpatent Literatures 5 or 6), and a high bactericidal activity is maintained in acidic electrolyzed water stored for a long time after generation (for example, see Nonpatent Literature 7).

CITATION LIST

Nonpatent Literature

Nonpatent Literature 1: Becking, L. G. M. B., Kaplan, I. R., Moore, D., "Limits of the natural environment in terms of pH and oxidation-reduction potentials", *J. Geolog.*, 1960, 68, p. 243-284

Nonpatent literature 2: Kunimoto Hotta, "Use of functional water—the bactericidal mechanism and applications of strongly acidic electrolyzed water", *Food Processing and Ingredients*, 33; 5-7, 1998

Nonpatent Literatures 3: Atsuo Iwasawa, Yoshiko Nakamura, "Bactericidal effect of acidic electrolyzed water—Comparison of chemical acidic sodium hydrochloride solution", *The journal of The Japanese Association for Infectious Diseases*, 70; 915-922, 1996

Nonpatent Literature 4: Katsura Tsuchiya, Kunimoto Hotta, "Chemistry of acidic electrolyzed water: A critical review on the chemical bactericidal factors of the acidic electrolyzed water" *Bulletin of Science and Engineering Takushoku University*, 9: 21-30, 2004

Nonpatent literature 5: Shigeaki Yonemori, et al., "Analysis of Hydroxyl Radical Generated In Electrolyzed Strong Acid Aqueous Solution by Electron Spin Resonance Spectroscopy" *Journal of The Chemical Society of Japan*, 7: 497-501, 1997

Nonpatent Literature 6: Hiroko Suzuki, el al., "Observation of Oxygenic Radicals in High Oxidation Potential Water" *The Japanese Journal of Conservative Dentistry*, 41: 975-982, 1998

Nonpatent Literature 7: Katsura Tsuchiya, Kunimoto Hotta, "Characterization of Chemical Factors as the Bactericidal Basis of Acidic DENKAISUI", *Kinousui Kenkyu*, 2: 75-80, 2004

SUMMARY OF INVENTION

Technical Problem

Sodium hypochlorite may damage mucous membrane and have adverse effects for a human body since it is alkaline. In contrast, strongly acidic electrolyzed water is safe for both people and the environment. Therefore, its further uses as a bactericidal washing agent are expected, and technologies to further enhance the bactericidal capacity and washing effect of strongly acidic electrolyzed water is desired to be developed.

The present invention is made in view of the above problems. An object of the present invention is to provide a bactericidal water generating system and a method of bactericidal washing, which can enhance the bactericidal capacity and washing effect of acidic electrolyzed water.

Solution to Problem

To achieve the above object, a bactericidal water generating system according to the present invention comprises an electrolyzer which electrolyzes an aqueous electrolyte solution containing a chloride to generate acidic electrolyzed water; an acidic water container connected to the electrolyzer so that the acidic electrolyzed water generated with the electrolyzer can be stored therein; and a gaseous chlorine circulator provided so that gaseous chlorine generated from the acidic electrolyzed water in the acidic water container is collected, and the gaseous chlorine collected is supplied to the acidic electrolyzed water in the acidic water container by bubbling.

A method of bactericidal washing according to the present invention comprises: electrolyzing an aqueous electrolyte solution containing a chloride with an electrolyzer to generate acidic electrolyzed water; collecting gaseous chlorine generated from the acidic electrolyzed water produced; supplying the gaseous chlorine collected to the acidic electrolyzed water by bubbling to generate bactericidal water; and washing an object with the bactericidal water.

The method of bactericidal washing according to the present invention can be suitably performed using the bactericidal water generated with the bactericidal water generating system according to the present invention. According to the present invention, acidic electrolyzed water may be strongly acidic electrolyzed water having pH 2.7 or below as well as electrolyzed water having pH 2.7 to 5 or weakly acidic electrolyzed water having pH 5 to 6.5. According to the bactericidal water generating system and the method of bactericidal washing according to the present invention, the concentration of hypochlorous acid dissolved in acidic electrolyzed water can be increased, and the bactericidal capacity due to the action of hypochlorous acid can be enhanced by collecting gaseous chlorine generated from acidic electrolyzed water and supplying the gaseous chlorine collected to the acidic electrolyzed water by bubbling. Further, bubbling not only can agitate acidic electrolyzed water but also can enhance the washing effect on an object. The gaseous chlorine circulator may be capable of adjusting the height or position of a gaseous chlorine feed inlet for acidic electrolyzed water by means of power or manual operation. In this case, gaseous chlorine may be directly sprayed to an object to enhance the washing effect.

According to the bactericidal water generating system and the method of bactericidal washing according to the present invention, the amount of hydrogen peroxide contained in acidic electrolyzed water generated by electrolysis can be increased by pre-adjusting a pH of an aqueous electrolyte solution to be electrolyzed to pH 3 to 5 with a pH adjuster. Therefore, the amount of hydroxyl radicals generated by adding a transition metal and DMSO to acidic electrolyzed water can be increased to enhance the washing effect. The pH adjuster preferably comprises an acid such as hydrochloric acid (HCl) and acetic acid ($CH_3COOH$).

The bactericidal water generating system according to the present invention preferably has a transition metal supply unit provided so that a transition metal-containing solution can be supplied into the inside of the acidic water container. The method of bactericidal washing according to the present invention preferably comprises: supplying a transition metal-containing solution to the bactericidal water generated; and then washing the object. In this case, the washing effect can be enhanced by the following principle.

That is, when an aqueous electrolyte solution containing a chloride is electrolyzed, hydrogen peroxide is supposedly generated in the anode side according to the following reaction formulas.

$$H_2O \rightarrow 2H^+ + \tfrac{1}{2}O_2 + 2e^-$$

$$2Cl^- \rightarrow Cl_2 + 2e^-$$

$$Cl_2 + H_2O \rightarrow HOCl + HCl$$

$$O_2 + e^- \rightarrow O_2^-$$

$$O_2^- + 2H^+ + e^- \rightarrow H_2O_2$$

If such hydrogen peroxide is present, by adding a transition metal such as divalent iron to this, the Fenton reaction as shown below occurs, and a hydroxyl radical (.OH) is generated.

$$H_2O_2 + Fe^{2+} \rightarrow .OH + OH^- + Fe^{3+}$$

For this reason, by supplying a transition metal to acidic electrolyzed water generated by electrolysis, not only the bactericidal capacity by hypochlorous acid but also the antimicrobial activity by hydroxyl radicals can be obtained to enhance the washing effect. In particular, bubbling can enhance the bactericidal effect by agitating a transition metal-containing solution in acidic electrolyzed water.

The bactericidal water generating system according to the present invention may have an additive supply unit provided so that a solution containing dimethyl sulfoxide (DMSO) or diethyl sulfoxide can be supplied to the inside of the acidic water container. The method of bactericidal washing according to the present invention may comprise supplying a solution containing dimethyl sulfoxide or diethyl sulfoxide to the bactericidal water after washing the object to generate second bactericidal water, and washing the object again with the second bactericidal water. In this case, the washing effect can be enhanced by the following principle. Note that the principle is described below for the case of dimethyl sulfoxide (DMSO), but it is also similar for the case of diethyl sulfoxide.

That is, as shown in FIG. 1(a), DMSO [$(CH_3)_2SO$] is known as a scavenger of hydroxyl radicals. However, since DMSO has an S=O double bond, polarization occurs in this part, showing a very large dipole moment. For this reason, as shown in FIG. 1(b), when it is added to acidic electrolyzed water in which hydrogen peroxide is present, $OH^-$ generated from the one-electron reduction reaction of hydrogen peroxide ($H_2O_2$) reacts with polarized DMSO. It is thought that this strongly promotes the one-electron-reduction reaction of hydrogen peroxide and enhances the generation of hydroxyl radicals (.OH).

Meanwhile since DMSO decomposes hypochlorous acid which is dissolved in acidic electrolyzed water, the bactericidal capacity by hypochlorous acid and the antimicrobial activity by hydroxyl radicals can not co-exist. For this reason, the washing effect can be enhanced by washing an object by taking advantage of the bactericidal capacity by hypochlorous acid dissolved in bactericidal water of acidic electrolyzed water, then adding DMSO to the bactericidal water to generate hydroxyl radicals, and washing the object again by taking advantage of the antimicrobial activity by hydroxyl radicals.

Note that DMSO, which is commonly used as a cell protective agent and the like, shows no adverse effect on human body, and is safe. Further, because hydrogen peroxide is no longer present in the bactericidal water in which hydroxyl radicals are generated via the Fenton reaction by supplying a transition metal to acidic electrolyzed water, addition of DMSO to this does not generate hydroxyl radicals, and DMSO functions as a scavenger of hydroxyl radicals. Further, because DMSO decomposes hypochlorous acid, the bactericidal water may be treated to give one comprising neither hypochlorous acid nor hydroxyl radicals. For this reason, a waste of the bactericidal water can be safely treated by adding DMSO to the bactericidal water after washing.

In the bactericidal water generating system according to the present invention, the electrolyzer preferably repeats an electrolysis of the electrolyzed water generated at the anode side for 1 to 2 times to generate the acidic electrolyzed water. In the method of bactericidal washing according to the present invention, the electrolyzer preferably repeats an electrolysis of the electrolyzed water generated at the anode side for 1 to 2 times to generate the acidic electrolyzed water. In this case, as lowering a pH of the acidic electrolyzed water for each time of performing electrolysis, the concentration of hypochlorous acid and the concentration of hydrogen peroxide in the acidic electrolyzed water can be increased. By this, the bactericidal capacity by hypochlorous acid and the washing effect by hydroxyl radicals generated by adding a transition metal and DMSO can be enhanced. Note that the amount of hydrogen peroxide can be increased by merely pre-adjusting a pH of an aqueous electrolyte solution to pH 3 to 5 with a pH adjuster, and therefore, the frequency of electrolysis can be reduced.

In the bactericidal water generating system according to the present invention, the aqueous electrolyte solution preferably contains at least either sodium chloride or potassium chloride as a chloride. In the method of bactericidal washing according to the present invention, the aqueous electrolyte solution preferably contains at least either sodium chloride or potassium chloride as a chloride. In this case, hypochlorous acid can be efficiently generated by electrolysis, and the bactericidal capacity can be enhanced.

In the method of bactericidal washing according to the present invention, the object may be medical devices, foodstuffs, cooking articles, any other articles. In a case where the object is a fishery product, harmful bacteria and viruses which may be contained in the fishery product can be killed and washed to increase food safety. In particular, in a case where the fishery product is oyster, Noro virus which may be contained in oyster can be killed to prevent viral food poisoning.

Advantageous Effects of Invention

According to the present invention, a bactericidal water generating system and a method of bactericidal washing which can enhance the bactericidal capacity and the washing effect of the acidic electrolyzed water can be provided.

BRIEF DESCRIPTION OF DRAWINGS

FIG. 1 shows (a) a chemical formula in a case where DMSO serves as a scavenger of hydroxyl radicals, and (b) chemical formulas in a case where DMSO is added to strongly acidic electrolyzed water in which hydrogen peroxide is present.

FIG. 10 shows graphs of (a) an ESR spectrum for strongly acidic electrolyzed water obtained by performing electrolysis for 3 times using a 1% aqueous solution of NaCl as an aqueous electrolyte solution with the bactericidal water generating system shown in FIG. 2, and (b) an ESR spectrum when 100 mM sodium formate was added to that strongly acidic electrolyzed water.

DESCRIPTION OF EMBODIMENTS

Below, embodiments of the invention will be described based on the drawings.

FIGS. 2 to 12 show the bactericidal water generating system and the method of bactericidal washing according to the embodiment of the invention.

Figure 2:
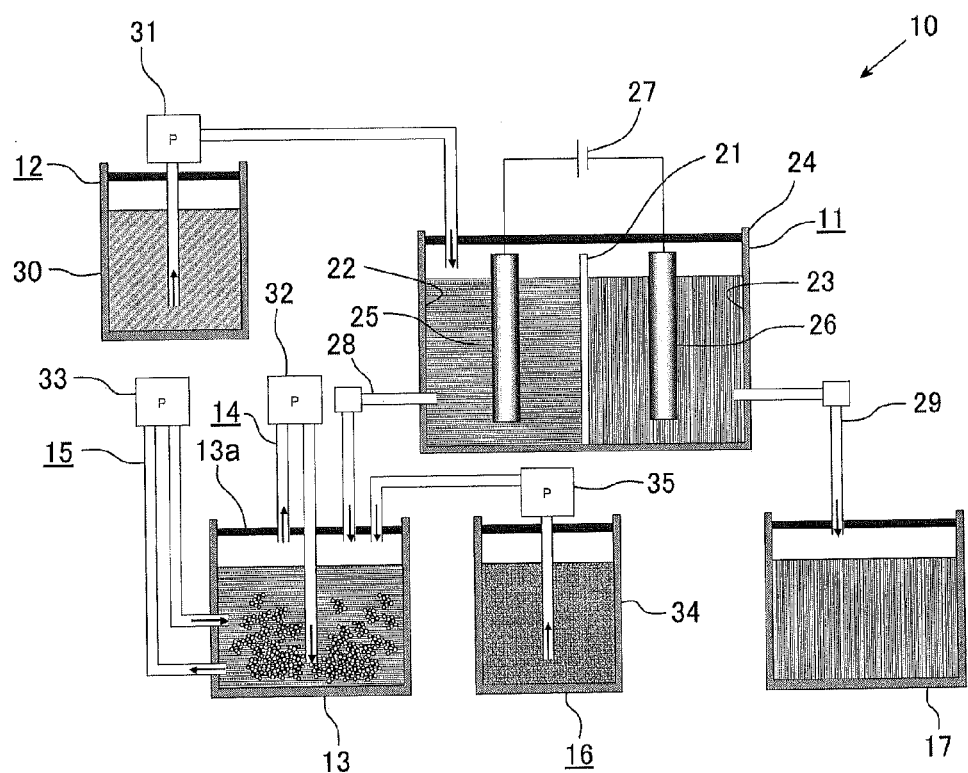
FIG. 2 shows a schematic side view illustrating a bactericidal water generating system according to an embodiment of the invention.

As shown in FIG. 2, a bactericidal water generating system 10 has an electrolyzer 11, a pH adjustment unit 12, an acidic water container 13, a gaseous chlorine circulator 14, an acidic water circulator 15, an additive supply unit (a transition metal supply unit) 16 and an alkaline water container 17.

The electrolyzer 11 has an electrolytic bath 24 divided into an anode chamber 22 and a cathode chamber 23 by a separating membrane 21, an anode 25 arranged in the anode chamber 22, a cathode 26 arranged in the cathode chamber 23 and a power supply 27 applying voltage between the anode 25 and the cathode 26. The electrolyzer 11 is configured to perform electrolysis by adding an aqueous electrolyte solution containing a chloride into the inside thereof, and applying voltage between the anode 25 and the cathode 26 by means of the power supply 27. In addition, it is configured so that this will generate acidic electrolyzed water in the anode chamber 22, and alkaline electrolyzed water in the cathode chamber 23. The acidic electrolyzed water generated may be strongly acidic electrolyzed water having pH 2.7 or below, electrolyzed water having pH 2.7 to pH 5.0 or weakly acidic electrolyzed water having pH 5.0 to 6.5. The electrolyzer 11 has an anode side drain line 28 and a cathode side drain line 29 provided at a lower portion of the anode chamber 22 and the cathode chamber 23, respectively so that the acidic electrolyzed water and the alkaline electrolyzed water generated can be drained.

Note that the aqueous electrolyte solution comprises an aqueous solution of sodium chloride, an aqueous solution of potassium chloride or mixed aqueous solutions thereof. Further, the electrolyzer 11 may be configured to have 2 to 3 electrolytic baths 24 so that electrolysis can be repeated for 2 to 3 times while the acidic electrolyzed water generated in the anode chamber 22 of each of the electrolytic baths 24 is transferred to the next electrolytic bath 24. In this case, the acidic electrolyzed water generated in the anode chamber 22 of the last electrolytic bath 24 will be drained from the anode side drain line 28.

The pH adjustment unit 12 has a pH adjuster container 30 for storing a pH adjuster, and a pump 31 for supplying the pH adjuster from the pH adjuster container 30 to the inside of the electrolytic bath 24. The pH adjustment unit 12 is configured to pre-adjust a pH of the aqueous electrolyte solution before electrolysis in the electrolytic bath 24 to pH 3 to 5 by supplying the pH adjuster to the electrolytic bath 24. Note that the pH adjuster preferably comprises hydrochloric acid (HCl), acetic acid ($CH_3COOH$) and an organic acid such as citric acid.

The acidic water container 13 is connected to the anode side drain line 28 of the electrolytic bath 24, and provided so that the acidic electrolyzed water generated by the electrolyzer 11 can be stored therein. The acidic water container 13 is sealed with a cover 13a to prevent leakage of gaseous chlorine generated from the stored acidic electrolyzed water to the outside. The gaseous chlorine circulator 14 has a pump 32, and is configured to collect gaseous chlorine generated from acidic electrolyzed water inside the acidic water container 13 with the pump 32, and to supply the gaseous chlorine collected to the acidic electrolyzed water inside the acidic water container 13 by bubbling. The gaseous chlorine circulator 14 may be capable of adjusting the height or position of a gaseous chlorine feed inlet for the acidic electrolyzed water by means of power or manual operation. In this case, gaseous chlorine may be directly sprayed to an object to increase the washing effect.

The acidic water circulator 15 has a pump 33, and is configured to collect the acidic electrolyzed water inside the acidic water container 13 with the pump 33, and to return it to the inside of the acidic water container 13 again. By this, the acidic water circulator 15 is capable of agitating acidic electrolyzed water so that gaseous chlorine may be effectively generated from the acidic electrolyzed water.

The additive supply unit (the transition metal supply unit) 16 has an additive container 34 for storing a transition metal-containing solution or a solution containing dimethyl sulfoxide (DMSO) or diethyl sulfoxide, and a pump 35 for supplying the transition metal-containing solution or the solution containing dimethyl sulfoxide (DMSO) or diethyl sulfoxide from the additive container 34 to the inside of the acidic water container 13. The additive supply unit 16 is capable of adding a transition metal, or dimethyl sulfoxide or diethyl sulfoxide to acidic electrolyzed water stored inside the acidic water container 13.

The alkaline water container 17 is connected to the cathode side drain line 29 of the electrolytic bath 24, and is provided so that alkaline electrolyzed water generated with the electrolyzer 11 can be stored therein.

The method of bactericidal washing according to an embodiment of the present invention can be suitably performed using bactericidal water generated by the bactericidal water generating system 10. That is, the method of bactericidal washing according to the first embodiment of the present invention comprises: first, electrolyzing an aqueous electrolyte solution containing a chloride with the electrolyzer 11 to generate acidic electrolyzed water; and storing the resulting acidic electrolyzed water in the acidic water container 13. Gaseous chlorine generated from acidic electrolyzed water inside the acidic water container 13 is collected with the gaseous chlorine circulator 14, and the gaseous chlorine collected is supplied to the acidic electrolyzed water by bubbling. Further, using the additive supply unit 16, a transition metal-containing solution is supplied to the acidic electrolyzed water inside the acidic water container 13 to generate bactericidal water. Then, the bactericidal water generated is used to wash an object. At this time, bubbling of gaseous chlorine not only can agitate the acidic electrolyzed water but also can enhance the washing effect for the object. Further, bubbling can agitate the transition metal-containing solution in the acidic electrolyzed water to enhance the washing effect for an object.

Further, the method of bactericidal washing according to the second embodiment of the present invention comprises: first, electrolyzing an aqueous electrolyte solution containing a chloride with the electrolyzer 11 to generate acidic electrolyzed water; and storing the resulting acidic electrolyzed water in the acidic water container 13. Gaseous chlorine generated from acidic electrolyzed water inside the acidic water container 13 is collected with the gaseous chlorine circulator 14, and the gaseous chlorine collected is supplied to the acidic electrolyzed water by bubbling to generate a first bactericidal water. The first bactericidal water generated is used to wash an object. At this time, bubbling of gaseous chlorine not only can agitate the acidic electrolyzed water but also can enhance the washing effect for the object. Further, using the additive supply unit 16, a solution containing dimethyl sulfoxide or diethyl sulfoxide is supplied to the first bactericidal water after washing the object to generate a second bactericidal water. Then, the second bactericidal water generated is used to wash the object again.

In the bactericidal water generating system 10 and the method of bactericidal washing according to the first and second embodiments of the present invention, the concentration of hypochlorous acid dissolved in acidic electrolyzed water can be increased, and the bactericidal capacity by the action of hypochlorous acid can be enhanced by collecting gaseous chlorine generated from acidic electrolyzed water and supplying the gaseous chlorine collected to the acidic electrolyzed water by bubbling.

In particular, in the method of bactericidal washing according to the first embodiment of the present invention, hydroxyl radicals can be generated by the Fenton reaction by supplying a transition metal to acidic electrolyzed water generated by electrolysis. By this, not only the bactericidal capacity by hypochlorous acid but also the antimicrobial activity by hydroxyl radicals can be obtained to enhance the washing effect. Further, in the method of bactericidal washing according to the first embodiment of the present invention, a waste of bactericidal water can be safely treated by adding dimethyl sulfoxide or diethyl sulfoxide to the bactericidal water after washing to transform the bactericidal water into one which contains neither hypochlorous acid nor hydroxyl radicals.

Further, in the method of bactericidal washing according to the second embodiment of the present invention, generation of hydroxyl radicals can be enhanced by supplying dimethyl sulfoxide or diethyl sulfoxide to acidic electrolyzed water generated by electrolysis. For this reason, the washing effect can be enhanced by washing an object by taking advantage of the bactericidal capacity of hypochlorous acid dissolved in the first bactericidal water of acidic electrolyzed water, and then washing the object again by taking advantage of the antimicrobial activity of hydroxyl radicals generated by adding dimethyl sulfoxide or diethyl sulfoxide to the first bactericidal water.

In the bactericidal water generating system 10 and the methods of bactericidal washing according to the first and second embodiments of the present invention, an amount of hydrogen peroxide contained in acidic electrolyzed water generated by electrolysis can be increased by pre-adjusting an aqueous electrolyte solution to pH 3 to 5 with a pH adjustment unit 12. Therefore, an amount of hydroxyl radicals generated by adding a transition metal and dimethyl sulfoxide or diethyl sulfoxide to acidic electrolyzed water can be increased to enhance the washing effect.

Further, by repeating electrolysis with the electrolyzer 11, as a pH of acidic electrolyzed water is decreased at each time of performing electrolysis, the concentration of hypochlorous acid and the hydrogen peroxide concentration in acidic electrolyzed water can be increased. By this, the bactericidal capacity of hypochlorous acid and the washing effect of hydroxyl radicals generated by adding a transition metal and dimethyl sulfoxide or diethyl sulfoxide can be enhanced.

The bactericidal water generating system 10 and the methods of bactericidal washing according to the first and second embodiments of the present invention use acidic electrolyzed water and a transition metal and dimethyl sulfoxide or diethyl sulfoxide. Therefore, they are safe for both human and the environment. For this reason, they can be used for any fields such as bactericidal treatments for agriculture, bactericidal treatments for livestock barns, bactericidal treatments for removing fishiness in a tsunami disaster area, bactericidal treatments for surgery, bactericidal treatments for cooking and bactericidal treatments for hospital rooms. In particular, when they are used for disinfecting fishery products, for example, oyster and the like, harmful bacteria and viruses such as Noro virus which may be contained in oyster can be killed/washed to prevent viral food poisoning, thereby increasing food safety.

Below, the bactericidal water generating system 10 and the method of bactericidal washing according to the embodiment of the present invention will be described based on Examples.

Example 1

Generation of Strongly Acidic Electrolyzed Water

Aqueous solutions of 0.10 (w/v) and 1% (w/v) sodium chloride (NaCl) were electrolyzed for 15 min. under the conditions of a rated voltage of AC 100 V, a rated current of 0.6 A using the electrolyzer 11 (Altech Co., Ltd., "Super Water mini"). Strongly acidic electrolyzed water generated at the anode side was electrolyzed for 2 or 3 times under the same conditions if desired. The resulting strongly acidic electrolyzed water was measured for pH, an oxidation-reduction potential and a chlorine concentration. For measuring pH, the oxidation-reduction potential and the chlorine concentration, a "D-53 electrode 9621C" from Horiba Ltd., a "D-53 electrode 9300" from Horiba Ltd. and a "high concentration residual chlorine meter HI95771" from Hanna Instruments were used respectively.

The results from measurements of physical properties for strongly acidic electrolyzed water electrolyzed for 1 to 3 times are shown in Tables 1 and 2. Table 1 shows the results in a case where the aqueous electrolyte solution was a 0.1% aqueous solution of NaCl, and Table 2 shows the results in a case where the aqueous electrolyte solution was a 1% aqueous solution of NaCl. Further, each measurement in the tables is a mean value from 2 measurements.

TABLE 1

Characteristic values of electrolyzed water obtained from a 0.1% aqueous solution of NaCl (the mean value from 2 measurements)

| Number of performed electrolysis | pH | Oxidation-reduction potential | Chlorine concentration (ppm) |
|---|---|---|---|
| 1 | 2.43 | 1179 | 66 |
| 2 | 2.29 | 1194 | 124 |
| 3 | 2.14 | 1202 | 180 |

TABLE 2

Characteristic values of electrolyzed water obtained from a 1% aqueous solution of NaCl (the mean value from 2 measurements)

| Number of performed electrolysis | pH | Oxidation-reduction potential | Chlorine concentration (ppm) |
|---|---|---|---|
| 1 | 2.51 | 1167 | 230 |
| 2 | 2.31 | 1179 | 390 |
| 3 | 2.16 | 1184 | 500 |

As shown in Tables 1 and 2, when the number of performed electrolysis was increased, the tendencies were observed in which pH shifted to the acidic side, and the oxidation-reduction potential and the chlorine concentration were increased. Further, observed was that the chlorine concentration particularly depends on the concentration of an electrolyte (NaCl).

[Measurements of ESR (Electron Spin Resonance) Spectra]

Next, ESR spectra were measured for strongly acidic electrolyzed water electrolyzed for 1 to 3 times. Measurements were performed as follows. First, 180 µl of strongly acidic electrolyzed water was transferred into a glass test tube, and 20 µl of 8.9 M 5,5-dimethyl-1-pyrroline N-oxide (DMPO, Dojindo Laboratories) was further added as a spin trap agent, stirred for 10 seconds, and then transferred into an ESR measurement cell to measure ESR spectra after 30 seconds. The ESR measurement conditions are as follows; fields weep: 330.5 to 340.5 mT, field modulation frequency: 100 kHz, field modulation width: 0.7 mT, amplitude: 500, sweep time: 2 min., time constant: 0.1 s, microwave frequency: 9.420 GHz and microwave power: 4 mW. Further, for quantification of DMPO—OH, ESR spectra obtained under similar conditions were compared using 20 µM of 4-hydroxy-2,2,6,6-tetramethylpiperidine (TEMPOL, Sigma Aldrich) as a standard sample to calculate a concentration of DMPO—OH.

Figure 3:
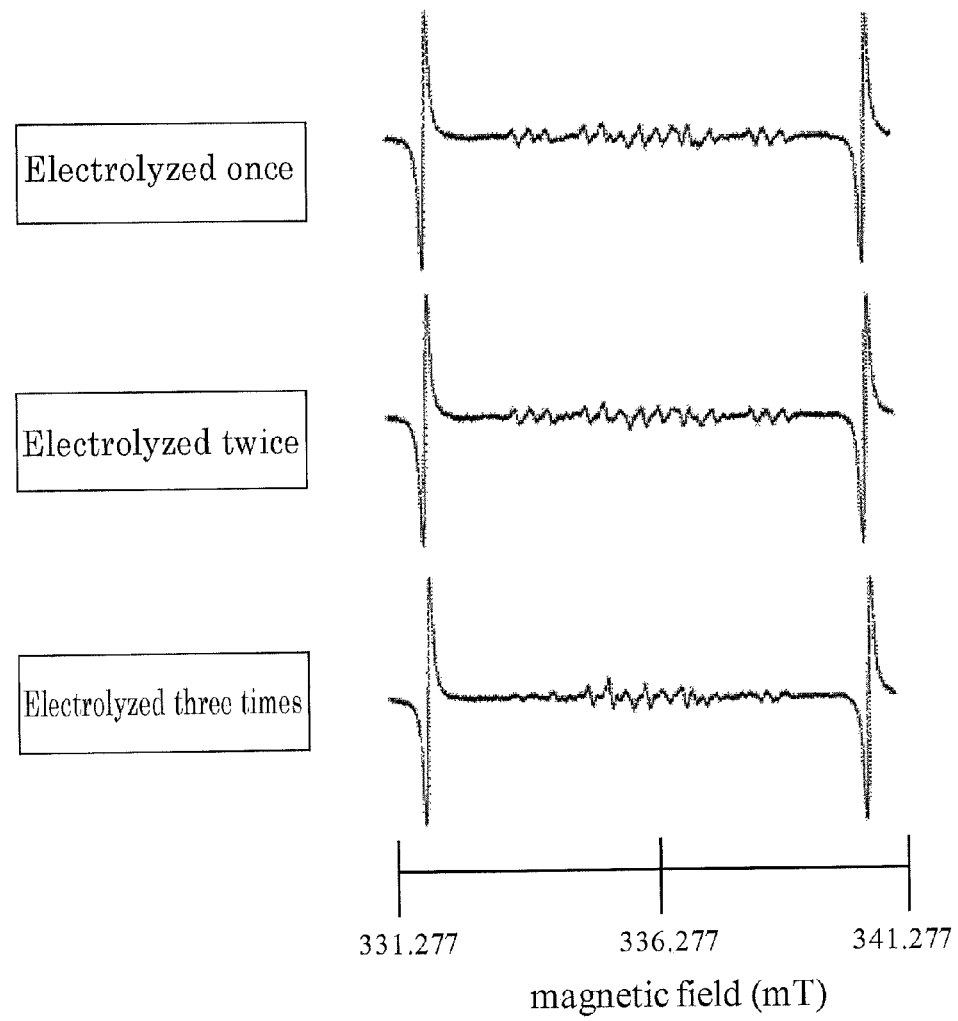
FIG. 3 shows graphs of ESR spectra for strongly acidic electrolyzed water obtained upon electrolysis using a 0.10 aqueous solution of NaCl as an aqueous electrolyte solution with the bactericidal water generating system shown in FIG. 2.
Figure 4:
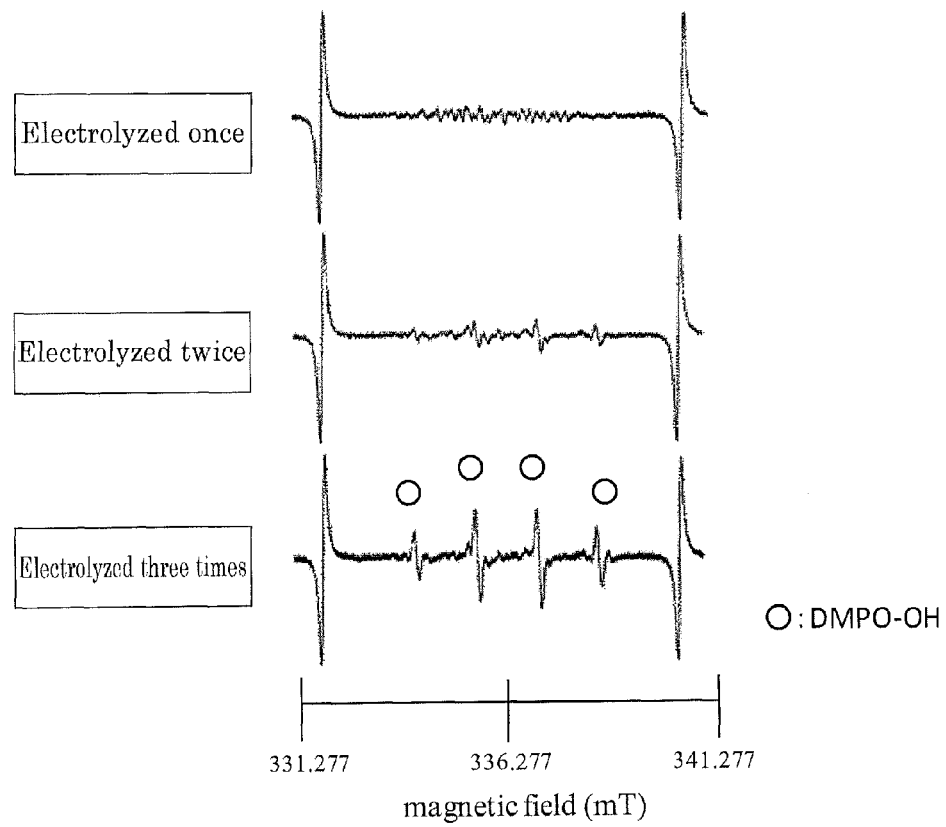
FIG. 4 shows graphs of ESR spectra for strongly acidic electrolyzed water obtained upon electrolysis using a 1% aqueous solution of NaCl as an aqueous electrolyte solution with the bactericidal water generating system shown in FIG. 2.

The results from ESR spectra measurements are shown in FIGS. 3 and 4. FIG. 3 shows the results in a case where the aqueous electrolyte solution was a 0.1% aqueous solution of NaCl and FIG. 4 shows the results in a case where the aqueous electrolyte solution was a 1% aqueous solution of NaCl. As shown in FIG. 3, in a case where a 0.1% aqueous solution of NaCl was used as an aqueous electrolyte solution, even when electrolysis was performed for 3 times, signals from DMPO—OH having intensities of 1:2:2:1 were not detected in the strongly acidic electrolyzed water. However, as shown in FIG. 4, in a case where the electrolyte concentration was increased to 1%, when electrolysis was repeated for 2, 3 times, intensified signals from DMPO—OH were observed. This indicates that depending on the chlorine concentration and the number of performed electrolysis, more hydroxyl radicals are generated.

Figure 5:
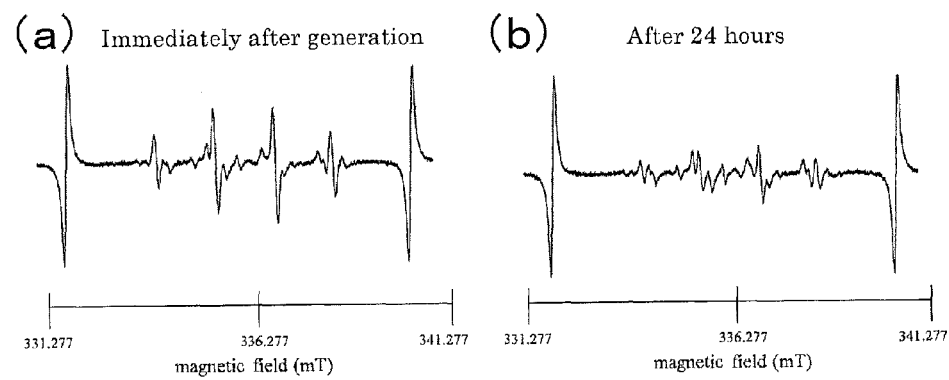
FIG. 5 shows graphs of ESR spectra: (a) immediately after and (b) 24 hours after the generation of strongly acidic electrolyzed water obtained by performing electrolysis for 3 times using 1% aqueous solution of NaCl as an aqueous electrolyte solution with the bactericidal water generating system shown in FIG. 2.

Generation of hydroxyl radicals was dependent on the chlorine concentration, which reveals that the reaction $2Cl^- \rightarrow Cl_2 + 2e^-$ contributes to the generation of hydroxyl radicals in the electrolysis at the anode side. Here, the result from the measurement of ESR spectrum after strongly acidic electrolyzed water generated by electrolyzing a to aqueous solution of NaCl for 3 times was stored for 24 hours under the room temperature and light-blocking conditions is shown in FIG. 5 together with the result before stored. As shown in FIG. 5, even when stored for 24 hours under the room temperature and light-blocking conditions, signals from DMPO—OH were detected although they were weaker, which indicated that hydroxyl radicals were stably generated.

[Induction of the Fenton Reaction]

The very short life time of hydroxyl radicals suggests that a production source of hydroxyl radicals is present in strongly acidic electrolyzed water. Accordingly, in order to show that the source is hydrogen peroxide, ferrous iron, which is a transition metal, was added to attempt to induce the Fenton reaction.

To do that, first, 20 µl of 8.9 M DMPO and 20 µl of 0.5 mM $FeSO_4$ were added to 180 µl of strongly acidic electrolyzed water obtained by electrolyzing a 1% aqueous solution of NaCl once, and stirred for 10 seconds, and then ESR spectrum was measured. The obtained ESR spectrum is shown in FIG. 6 together with the ESR spectrum after electrolyzing once.

Figure 6:
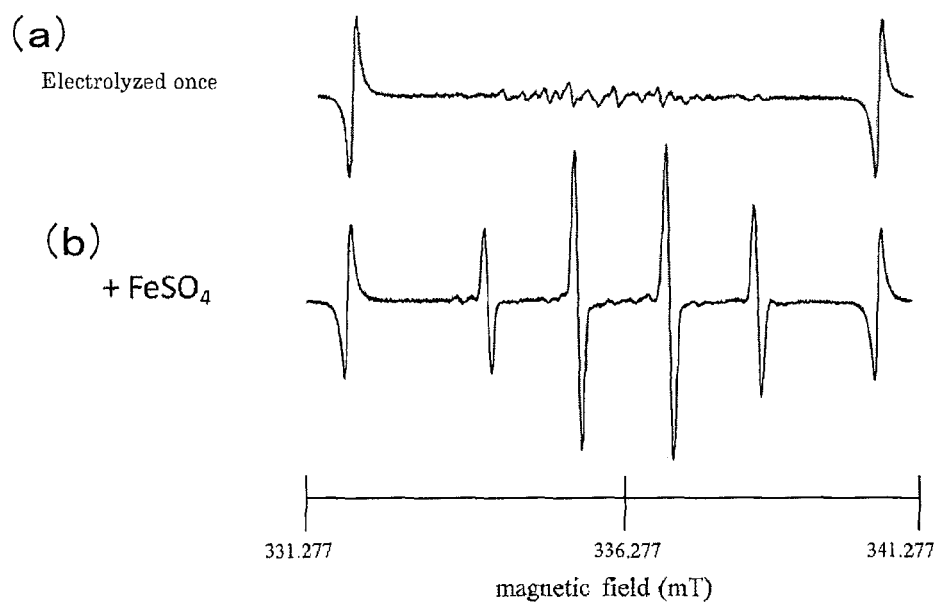
FIG. 6 shows graphs of ESR spectra for (a) strongly acidic electrolyzed water obtained by performing electrolysis once using 1% aqueous solution of NaCl as an aqueous electrolyte solution with the bactericidal water generating system shown in FIG. 2, and (b) when $FeSO_4$ was added to that strongly acidic electrolyzed water.

As shown in FIG. 6, when $FeSO_4$ was added as ferrous iron, appearance of very strong signals from DMPO—OH was observed. These signals were significantly attenuated by DMSO, a scavenger of hydroxyl radicals, which indicated that they were from hydroxyl radicals generated by the reaction of hydrogen peroxide present in the strongly acidic electrolyzed water with ferrous iron. Similar results were also obtained when a 0.1% aqueous solution of NaCl was used as an aqueous electrolyte solution, which indicated that hydrogen peroxide is present in strongly acidic electrolyzed water.

Figure 7:
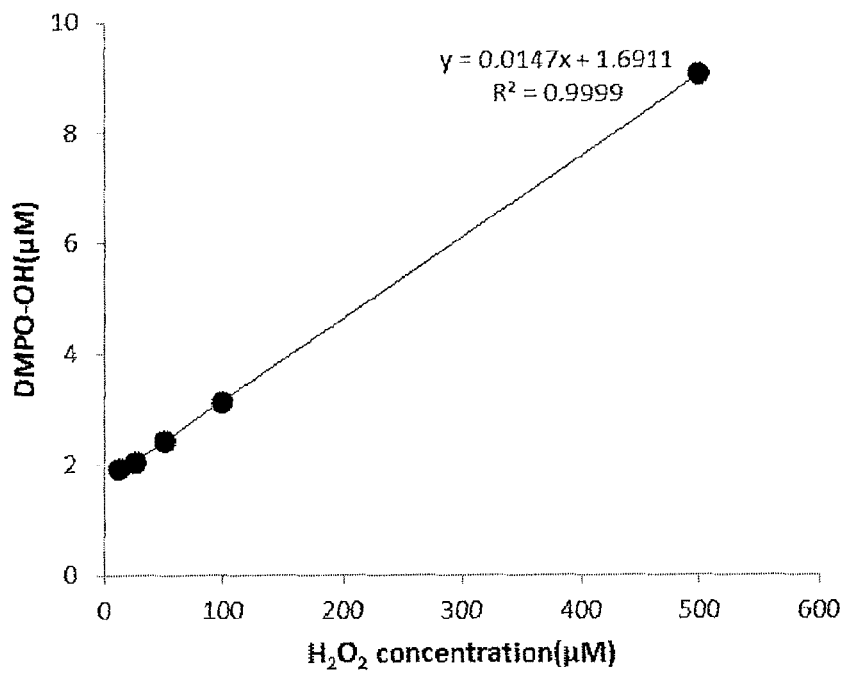
FIG. 7 shows a graph of a calibration curve for calculating a concentration of hydrogen peroxide in strongly acidic electrolyzed water from the concentration of DMPO—OH obtained from ESR data.

In order to compute a concentration of hydrogen peroxide (a $H_2O_2$ concentration) in strongly acidic electrolyzed water from the ESR data obtained, 20 µl of 8.9 M DMPO and 20 µl of 0.5 mM $FeSO_4$ were added to 180 µl of a hydrogen peroxide solution of a known concentration, stirred for 10 seconds, and then ESR spectra were measured in a similar fashion. The concentrations of DMPO—OH obtained were used to create a calibration curve. The calibration curve created is shown in FIG. 7. Further, the concentrations of hydrogen peroxide contained in strongly acidic electrolyzed water when a 1% aqueous solution of NaCl was electrolyzed for 3 times were computed using the calibration curve shown in FIG. 7. The results are shown in Table 3.

TABLE 3

Concentration of hydrogen peroxide in acidic electrolyzed water generated using a 1% aqueous solution of NaCl as an electrolytic solution

| Number of performed electrolysis | Concentration of hydrogen peroxide (µM) |
| --- | --- |
| 1 | 101.1 ± 11.7 |
| 2 | 219.2 ± 7.8 |
| 3 | 303.1 ± 13.1 |

Mean-value ± standard deviation (n = 3)

As shown in Table 3, as the number of performed electrolysis was increased, increased concentrations of hydrogen peroxide were observed. The results in Tables 1 and 2 show that a concentration of chlorine tends to increase as the number of performed electrolysis is increased, which can suggest that the amount of hydrogen peroxide in strongly acidic electrolyzed water depends on the concentration of chlorine, i.e., the reaction: $2Cl^- \rightarrow Cl_2 + 2e^-$.

[Addition of Acid to Aqueous Electrolyte Solution: In the Case of Adding Acid at Each Time of Performing Electrolysis]

The results in Table 2 suggest a possibility that generation of hydrogen peroxide and hydroxyl radicals may be dependent not only on the concentration of chlorine but also pH. In order to confirm this pH dependence, acid was added to an aqueous electrolyte solution to lower pH in advance before electrolysis, and ESR analysis was conducted for strongly acidic electrolyzed water obtained by electrolyzing that aqueous electrolyte solution. The results from the analysis are shown in FIG. 8 as compared with the case of no addition of acid.

Figure 8A:
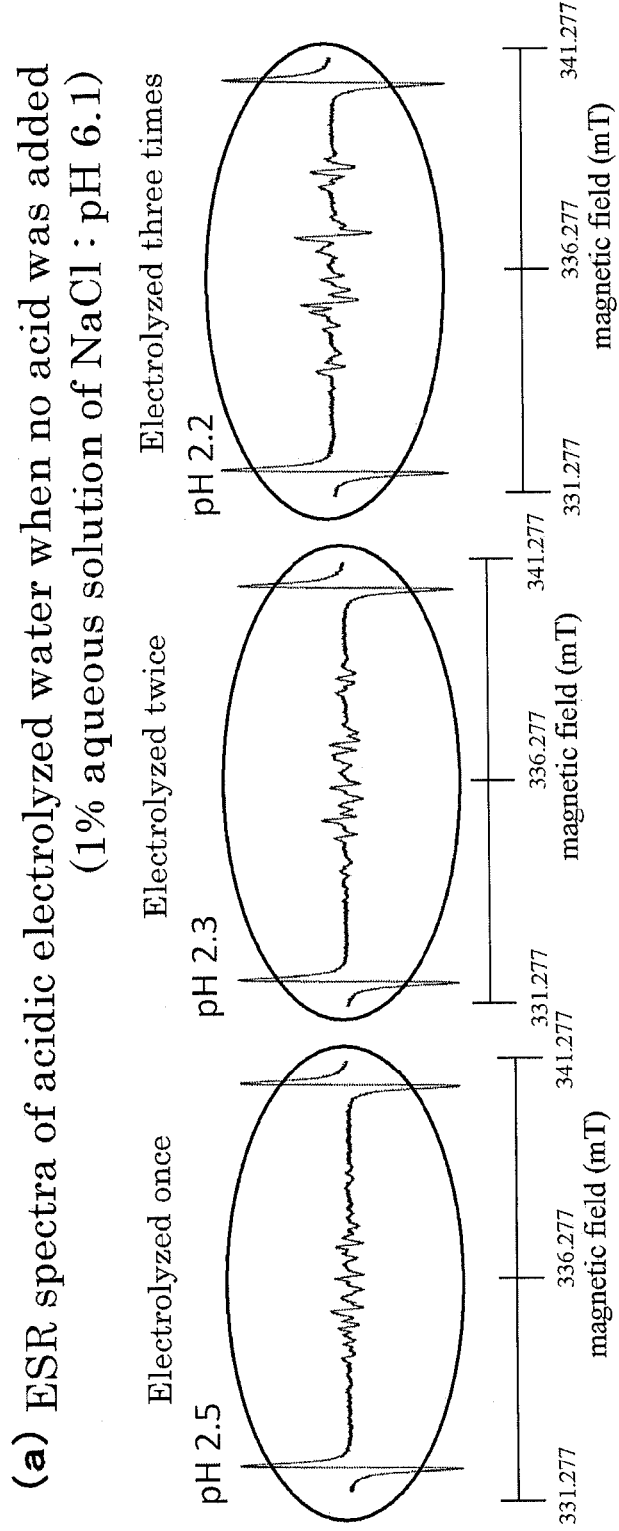
FIG. 8 shows graphs of (a) ESR spectra for strongly acidic electrolyzed water obtained by performing electrolysis using a 1% aqueous solution of NaCl as an aqueous electrolyte solution with the bactericidal water generating system shown in FIG. 2, (b) ESR spectra when hydrochloric acid was added to the strongly acidic electrolyzed water after electrolysis at each time of performing electrolysis and (c) ESR spectra when acetic acid was added to the strongly acidic electrolyzed water after electrolysis at each time of performing electrolysis.
Figure 8B:
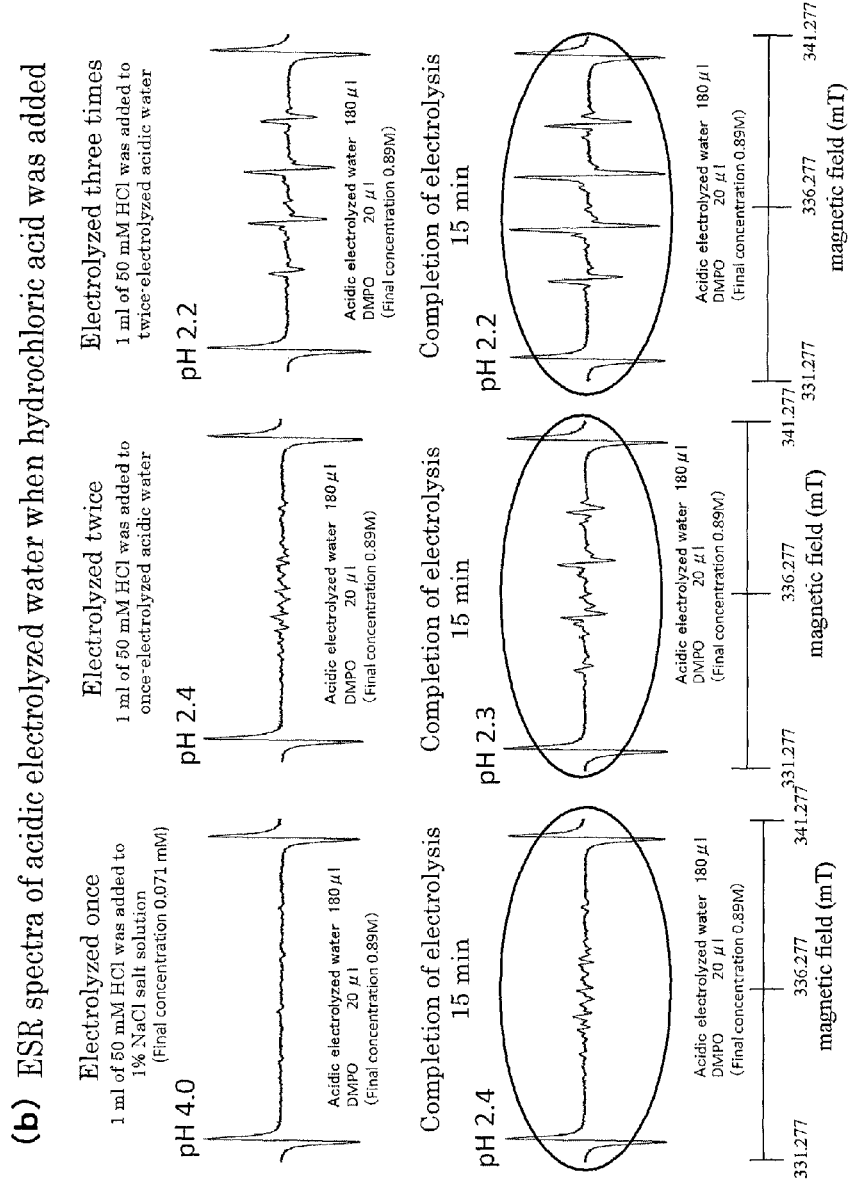
Figure 8C:
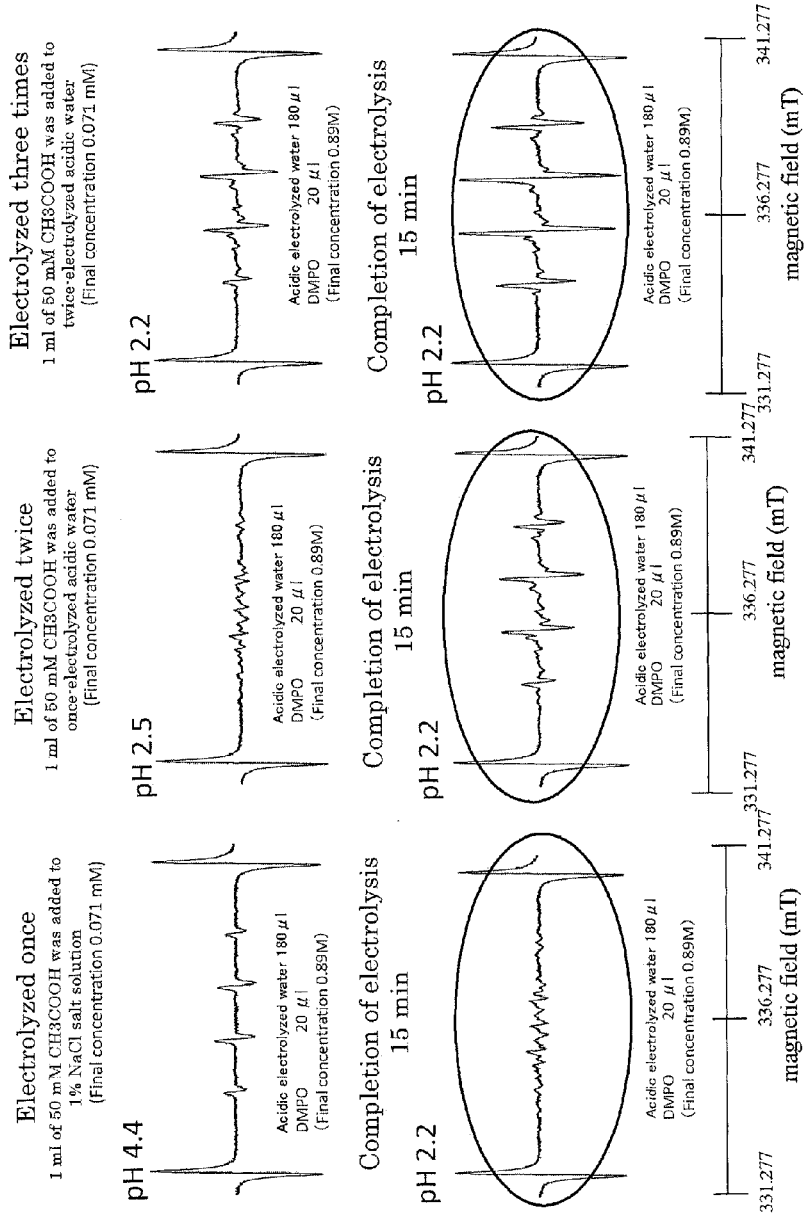

As shown in FIG. 8, when pH was lowered in advance with hydrochloric acid or acetic acid before electrolysis, enhanced signal intensities of DMPO—OH were observed as compared with a case where pH was not lowered. From this, the present inventors have discovered that the amount of hydroxyl radicals via hydrogen peroxide can be increased by lowering a pH of strongly acidic electrolyzed water with a pH adjuster such as acid. In other words, the present inventors have discovered that the concentration of chlorine as well as pH are effective measures to confer a hydroxyl radical activity on strongly acidic electrolyzed water.

[Addition of Acid to Aqueous Electrolyte Solution: In the Case of No Re-Addition of Acid]

A pH was adjusted to 3 to 5 by adding hydrochloric acid (HCl) or acetic acid ($CH_3COOH$) to an aqueous electrolyte solution, and electrolysis was performed twice without re-addition of acid. For strongly acidic electrolyzed water obtained by electrolysis, signals from DMPO—OH which is a spin adduct of a hydroxyl radical were analyzed by the electron spin resonance (ERS) method.

As experiment samples, samples were prepared in which pure water, 50 mM of $CH_3COOH$ (Wako Pure Chem Industries, Ltd.) and 50 mM HCl (Wako Pure Chem Industries, Ltd.) were added to 700 ml of a 1% aqueous solution of NaCl in an amount of 3 ml each. A pH of each sample was measured with a pH meter ("SG-2", Mettler-Toledo), and then electrolysis was performed twice for 15 min. under the conditions of a rated voltage of AC 100 V and a rated current of 0.6 A using an electrolyzer ("Super Water mini," Altech Co., Ltd.). ESR spectra for the strongly acidic electrolyzed water obtained were measured after performing electrolysis twice. The results from the measurements are shown in FIG. 9 as compared with a case in which pure water was added instead of acid.

Figure 9:
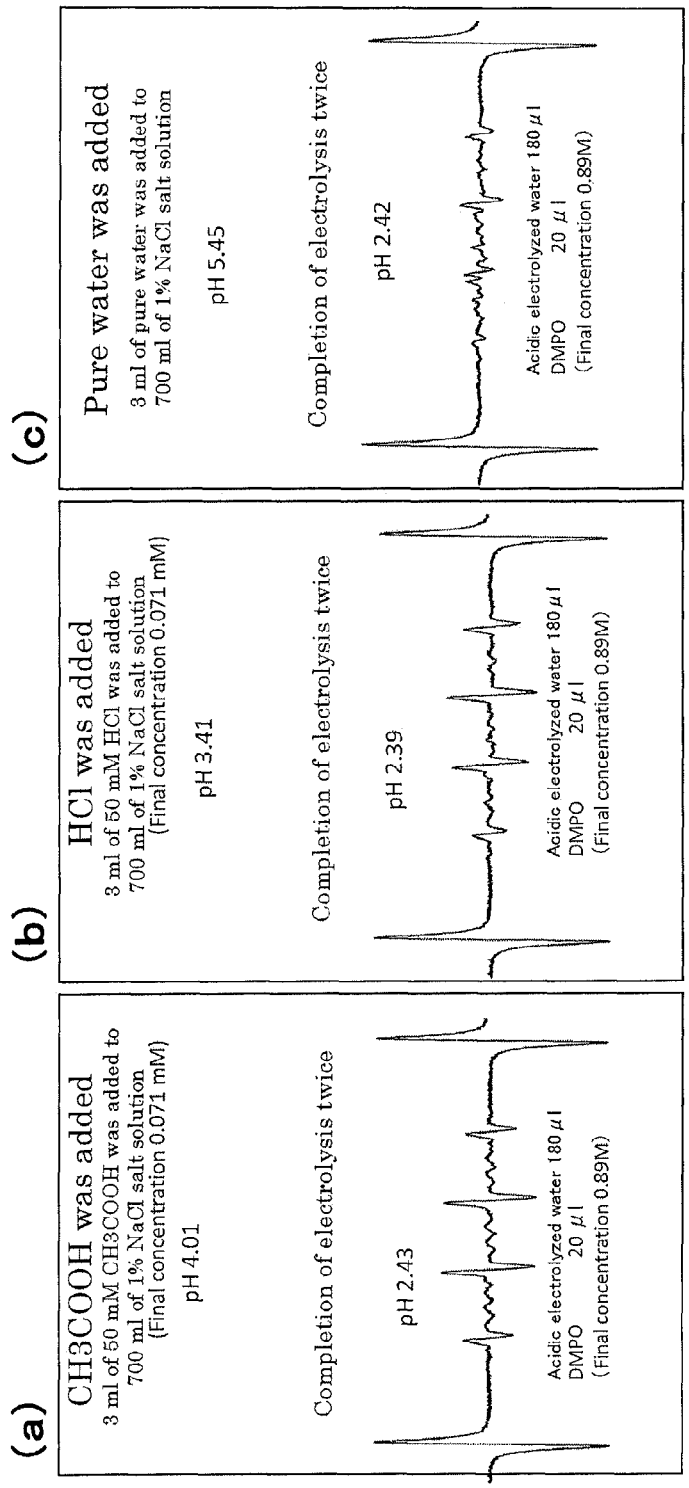
FIG. 9 shows graphs of (a) an ESR spectrum when acetic acid was added to an aqueous electrolyte solution to give a pH of 3 to 5, and then electrolysis was performed twice without further adding acid with the bactericidal water generating system shown in FIG. 2, (b) an ESR spectrum when hydrochloric acid was added to an aqueous electrolyte solution to give a pH of 3 to 5, and then electrolysis was performed twice without further adding acid and (c) an ESR spectrum when pure water was added to an aqueous electrolyte solution, and then electrolysis was performed twice.

As shown in FIG. 9, by performing electrolysis twice after adding HCl or $CH_3COOH$ to adjust a pH to 3 to 5, signals from DMPO—OH showing an intensity ratio of 1:2:2:1 were clearly enhanced as compared with a case in which only pure water was added and no acid was added, indicating that the amount of hydroxyl radicals generated was increased. This suggests that by pre-adjusting an aqueous electrolyte solution to pH 3 to 5 with a pH adjuster, the amount of hydrogen peroxide contained in acidic electrolyzed water generated by electrolysis can be increased.

[Generation of Hydroxyl Radicals by Adding DMSO]

Figure 11:
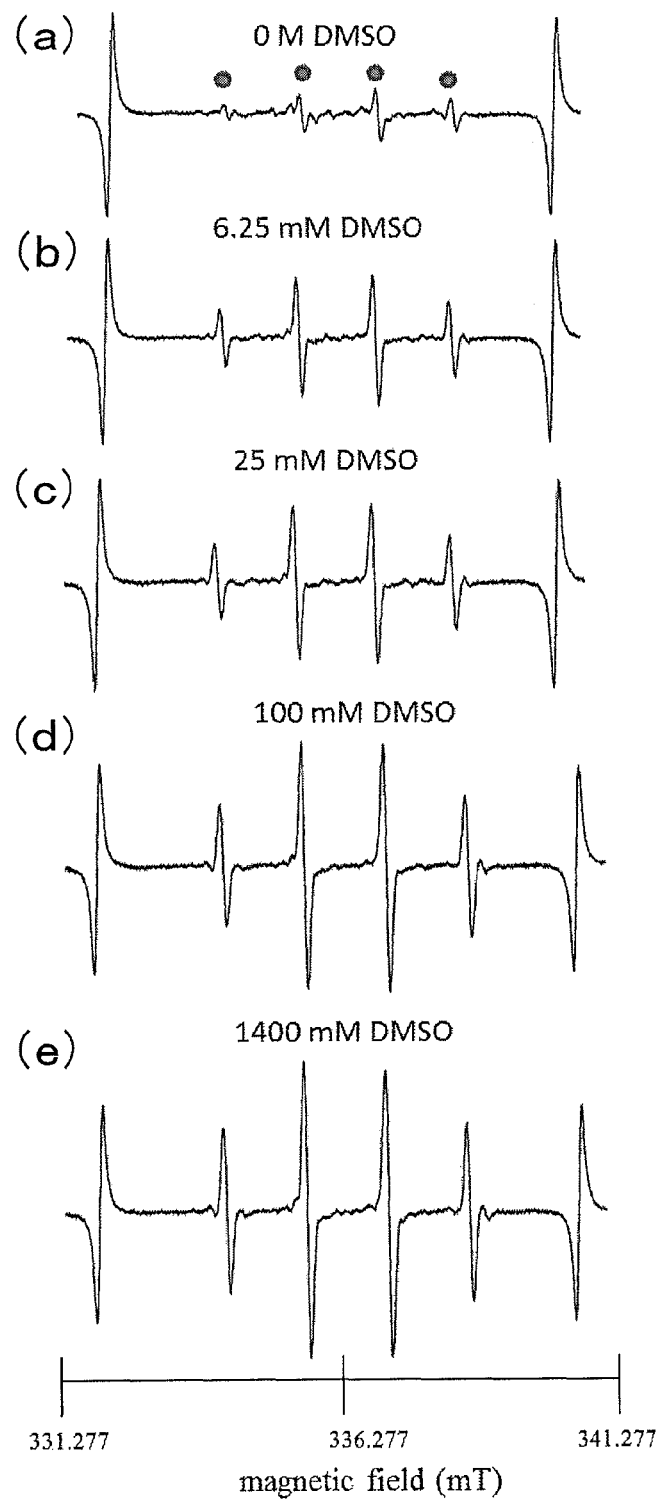
FIG. 11 shows graphs of (a) an ESR spectrum for strongly acidic electrolyzed water obtained by performing electrolysis for 3 times using a 1% aqueous solution of NaCl as an aqueous electrolyte solution with the bactericidal water generating system shown in FIG. 2, and ESR spectra when (b) 6.25 mM, (c) 25 mM, (d) 100 mM, (e) 1400 mM DMSO was added to that strongly acidic electrolyzed water.
Figure 12:
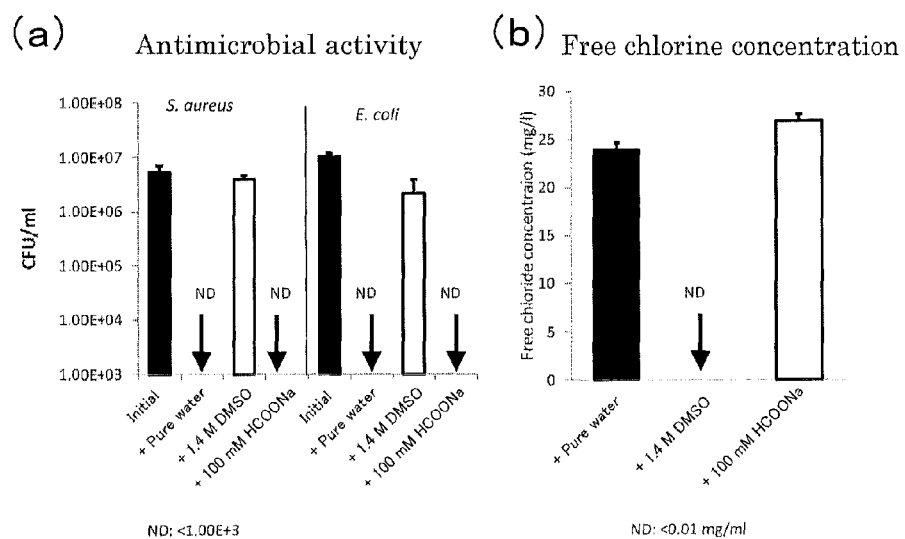
FIG. 12 shows graphs in which (a) the antimicrobial activity and (b) the concentration of free chlorine when a scavenger of hydroxyl radicals was added to strongly acidic electrolyzed water obtained by performing electrolysis once using a 0.1% aqueous solution of NaCl as an aqueous electrolyte solution with the bactericidal water generating system shown in FIG. 2.

In order to show that DMPO—OH detected in strongly acidic electrolyzed water obtained by electrolyzing a 1% aqueous solution of NaCl for 3 times as shown in FIG. 4 was originated from hydroxyl radicals, the effects of addition of sodium formate (Wako Pure Chemical Industries, Ltd.) which is a scavenger of hydroxyl radicals, and of dimethyl sulfoxide (DMSO, Wako Pure Chemical Industries, Ltd.)

were investigated. To do this, 100 mM of 8.9 M sodium formate or 20 ul of 6.25 mM, 25 mM, 100 mM, 1400 mM DMSO was added to 180 μl of strongly acidic electrolyzed water, and then ESR spectra were measured. The results from each measurement are shown in FIGS. 10 and 11.

As shown in FIG. 10, when sodium formate was added, complete disappearance of the DMPO—OH signals was observed, strongly suggesting that these signals was from hydroxyl radicals. However, in contrast, as shown in FIG. 11, when DMSO was added, enhanced signals from DMPO—OH was observed, and the concentration dependent enhancement of the signals was further observed. These results indicate that DMSO acts as an agent for enhancing generation of hydroxyl radicals, but not as a scavenger of hydroxyl radicals in strongly acidic electrolyzed water.

[Antimicrobial Activity Against Spore Bacterium]

Solutions obtained by adding 0.05 ml of 0.5 mM $FeSO_4$ to 0.95 ml of strongly acidic electrolyzed water obtained by electrolyzing a 1% aqueous solution of NaCl once, and of strongly acidic electrolyzed water obtained by electrolyzing a 0.1% aqueous solution of NaCl for 3 times were studied for the antimicrobial activity against a spore bacterium. For a test bacterium, a spore forming bacterium *Bacillus subtilis* JCM 1465 was used. The test bacterium was collected from a Petri dish cultured at 37° C. for 1 week in the Brain Heart Infusion (BHI) agar medium (Becton Dickinson), and heated at 65° C. for 30 min., and then stored at 4° C. before use. The stored bacterium liquid was adjusted to 1.0 to $3.0 \times 10^8$/ml using a bacterium turbidity standard liquid (Eiken Chemical Co., Ltd.) to give a test bacterium liquid.

A solution obtained by inoculating and mixing 1 ml of strongly acidic electrolyzed water obtained by electrolyzing a 1% aqueous solution of NaCl once with 10 μl of the test bacterium liquid, and a solution obtained by inoculating and mixing a solution obtained by adding 0.05 ml of 0.5 mM $FeSO_4$ to 0.95 ml of strongly acidic electrolyzed water obtained by electrolyzing a 0.1% aqueous solution of NaCl for 3 times with 10 μl of the test bacterium liquid were prepared, and 10 μl of each was collected over time, and added to 1 ml of the BHI liquid medium (Becton Dickinson). Then whether the bacterium grew or not was visually determined after cultured at 37° C. for 2 to 5 days. The results are shown in Table 4.

TABLE 4

Antimicrobial activity of various types of electrolyzed water on a spore bacterium *Bacillus subtilis*

|  | Acidic electrolyzed water (electrolyzed once) | Acidic electrolyzed water (electrolyzed for 3 times) + $FeSO_4$ |
|---|---|---|
| Initial | (+++) | (+++) |
|  | (+++) | (+++) |
|  | (+++) | (+++) |
| After 1 minute | (+++) | (+) |
|  | (++) | (−) |
|  | (++) | (−) |
| After 3 minutes | (+++) | (−) |
|  | (−) | (−) |
|  | (−) | (−) |

Determination of bacterial growth
(+++): Significant growth,
(++): Moderate growth
(+): Slight growth,
(−): Bacterium-negative As shown in Table 4, in a case where the strongly acidic electrolyzed water obtained by electrolyzing a 0.1% aqueous solution of NaCl once was used, bacterial growth showed almost no inhibition. Although 2 out of 3 samples became negative for the bacterium under the conditions of 3 min. exposure, one sample did not show growth inhibition at all. On the other hand, in the case of the solution in which ferrous iron ($FeSO_4$) was added to the strongly acidic electrolyzed water obtained by performing electrolysis for 3 times, the followings were observed: when 1 min. exposure, 1 out of 3 samples already showed significant growth inhibition, and 2 samples became completely negative for the bacterium; when 3 min. exposure, all of the 3 samples became negative for the bacterium. As described above, in the case of the solution in which ferrous iron ($FeSO_4$) was added to the strongly acidic electrolyzed water obtained by performing electrolysis for 3 times, an enhanced antimicrobial activity against the spore bacterium was clearly observed.

[Effects of Hydroxyl Radical Scavenger on Antimicrobial Activity and Free Chlorine Concentration of Strongly Acidic Electrolyzed Water]

In order to study the effects of a hydroxyl radical scavenger on the antimicrobial activity and free chlorine concentration of strongly acidic electrolyzed water, tests for the antimicrobial activity and measurements of a free chlorine concentration were performed. First, *Staphylococcus aureus* JCM2413 and *Escherichia coli* JCM5491 (Riken BioResource Center) were used as test bacteria. A solution obtained by electrolyzing a 0.1% (w/v) aqueous solution of NaCl once was used for strongly acidic electrolyzed water. As a hydroxyl radical scavenger, dimethyl sulfoxide (DMSO, Wako Pure Chemical Industries, Ltd.) and sodium formate (HCOONa, Wako Pure Chemical Industries, Ltd.) were used.

In antimicrobial activity tests, these bacteria were cultured at 37° C. overnight in the brain heart infusion (BHI) agar medium (Becton Dickinson), and then suspended in a sterilized physiological saline solution and adjusted to 1.0 to $3.0 \times 10^8$/mL to give a sample bacterium liquid. Mixed were 10 μL of each sample bacterium liquid, 100 μL of an additive (pure water, 14 M DMSO or 1 M HCOONa) and 890 μL of the strongly acidic electrolyzed water for 5 seconds. The resulting mixture was added to 1 mL of the BHI liquid medium. Form this, 200 μL was collected to apply on the BHI agar medium, and cultured at 37° C. for 2 days. Then the number of grown colonies (unit: CFU/ml) was counted. The results from the measurements are shown in FIG. 12(a).

Next, 1 volume of an additive (pure water, 14 M DMSO or 1M HCOONa) was added to 9 volumes of the strongly acidic electrolyzed water, and stirred. Then a free chlorine concentration was measured by the DPD method. The results from the measurements are shown in FIG. 12(b).

As shown in FIG. 12(a), the antimicrobial activity tests showed that the viable cell count was reduced by 3 or more orders of magnitude relative to the early viable cell count (primary count) for both *S. aureus* and *E. coli* in the case of the strongly acidic electrolyzed water in which pure water was added. Further, in a case where DMSO, a hydroxyl radical scavenger, was added in a final concentration of 1.4 M, there was almost no decrease in the viable cell count, indicating that the antimicrobial activity of the strongly acidic electrolyzed water was lost. In contrast, in a case where HCOONa, a hydroxyl radical scavenger, was added in a final concentration of 100 mM, a decreased viable cell count by 3 or more orders of magnitude was observed, indicating that the antimicrobial activity of the strongly acidic electrolyzed water was not affected.

In this context, assuming that the antimicrobial activity of the strongly acidic electrolyzed water were lost because hydroxyl radicals disappeared by addition of DMSO, a source of the activity of the strongly acidic electrolyzed water would be hydroxyl radicals. However, even when hydroxyl radicals disappeared by HCOONa which is another hydroxyl radical scavenger, the antimicrobial activity of the strongly acidic electrolyzed water was not affected. Therefore, hydroxyl radicals appear not to be a source of the activity of the strongly acidic electrolyzed water.

Next, when the free chlorine concentration was measured, as shown in FIG. 12(b), the results showed the free chlorine concentration became less than the detection limit (ND) by addition of DMSO. The results support that hypochlorous acid disappeared, and the antimicrobial activity of the strongly acidic electrolyzed water was lost by addition of DMSO. As reinforcing this, addition of HCOONa did not affect the free chlorine concentration, i.e., hypochlorous acid, and therefore, did not affect the antimicrobial activity of the strongly acidic electrolyzed water. From these results, a source of the antimicrobial activity of the strongly acidic electrolyzed water appears not to be a hydroxyl radical but hypochlorous acid.

DESCRIPTION OF REFERENCE NUMERALS

10 Bactericidal water generating system
11 Electrolyzer
21 Separating Membrane
22 Anode Chamber
23 Cathode Chamber
24 Electrolytic Bath
25 Anode
26 Cathode
27 Power Supply
28 Anode side drain line
29 Cathode side drain line
12 pH Adjustment unit
30 pH Adjuster container
31 Pump
13 Acidic water container
14 Gaseous chlorine circulator
32 Pump
15 Acidic water circulator
33 Pump
16 Additive supply unit (Transition metal supply unit)
34 Additive container
35 Pump
17 Alkaline water container

The invention claimed is:

1. A method of bactericidal washing, the method comprising: pre-adjusting a chloride-containing aqueous electrolyte solution to pH 3 to 5 with a pH adjuster; electrolyzing the aqueous electrolyte solution with an electrolyzer to generate acidic electrolyzed water; collecting gaseous chlorine generated from the resulting acidic electrolyzed water; supplying the gaseous chlorine collected to the acidic electrolyzed water by bubbling to generate bactericidal water; washing an object with the bactericidal water; and supplying a dimethyl sulfoxide- or diethyl sulfoxide-containing solution to the bactericidal water after washing.

2. The method of bactericidal washing according to claim 1, comprising: supplying a transition metal-containing solution to the bactericidal water generated, and then washing the object therewith.

3. The method of bactericidal washing according to claim 1, wherein the aqueous electrolyte solution contains at least either sodium chloride or potassium chloride as the chloride.

4. The method of bactericidal washing according to claim 1, wherein the object is a fishery product.

5. The method of bactericidal washing according to claim 1, wherein the acidic electrolyzed water has a pH of 2.7 or below.

6. The method of bactericidal washing according to claim 1, wherein the acidic electrolyzed water has a pH of 2.7 to 5.

7. The method of bactericidal washing according to claim 1, wherein the acidic electrolyzed water has a pH of 5 to 6.5.

8. A method of bactericidal washing, the method comprising: pre-adjusting a chloride-containing aqueous electrolyte solution to pH 3 to 5 with a pH adjuster; electrolyzing the aqueous electrolyte solution with an electrolyzer to generate acidic electrolyzed water; collecting gaseous chlorine generated from the resulting acidic electrolyzed water; supplying a dimethyl sulfoxide- or diethyl sulfoxide-containing solution to the acidic electrolyzed water generated by electrolysis; supplying the gaseous chlorine collected to the acidic electrolyzed water by bubbling to generate bactericidal water; and washing an object with the bactericidal water.

9. The method of bactericidal washing according to claim 8, comprising: supplying a transition metal-containing solution to the bactericidal water generated, and then washing the object therewith.

10. The method of bactericidal washing according to claim 8, wherein the aqueous electrolyte solution contains at least either sodium chloride or potassium chloride as the chloride.

11. The method of bactericidal washing according to claim 8, wherein the object is a fishery product.

12. The method of bactericidal washing according to claim 8, wherein the acidic electrolyzed water has a pH of 2.7 or below.

13. The method of bactericidal washing according to claim 8, wherein the acidic electrolyzed water has a pH of 2.7 to 5.

14. The method of bactericidal washing according to claim 8, wherein the acidic electrolyzed water has a pH of 5 to 6.5.

* * * * *